United States Patent [19]

Horio et al.

[11] Patent Number: 5,262,433
[45] Date of Patent: Nov. 16, 1993

[54] TETRAZOLEACETIC ACID DERIVATIVES AND METHOD OF ALDOSE REDUCTASE INHIBITION THEREWITH

[75] Inventors: Yoshihiro Horio, Hatano; Yasuhiro Ootake, Minamiashigara; Shohei Sawaki, Kanagawa; Sinji Inukai, Hatano; Mitsuji Agata, Kanagawa; Manami Umezawa, Atsugi; Masayoshi Goto, Isehara, all of Japan

[73] Assignee: Wakamoto Pharmaceutical Co., Ltd., Tokyo, Japan

[21] Appl. No.: 924,453

[22] Filed: Aug. 4, 1992

[30] Foreign Application Priority Data

Aug. 6, 1991 [JP] Japan ................... 3-219274

[51] Int. Cl.$^5$ ............ C07D 257/04; C07D 407/04; C07D 409/04; A61K 31/41
[52] U.S. Cl. ................ 514/381; 514/382; 548/253
[58] Field of Search ............ 548/253; 514/381, 382

[56] References Cited

U.S. PATENT DOCUMENTS 4,937,253  6/1990  Gleason et al. .......... 514/381
5,068,239  11/1991 Inukai et al. ........... 514/381

FOREIGN PATENT DOCUMENTS 0388967  3/1990  European Pat. Off. ........ 257/4
0421365  10/1990 European Pat. Off. ........ 409/4
0495526  1/1992  European Pat. Off. ........ 257/4
2082584  8/1980  United Kingdom ........... 514/381

Primary Examiner—David B. Springer
Attorney, Agent, or Firm—Burns, Doane, Swecker & Mathis

[57] ABSTRACT

A tetrazoleacetic acid derivative represented by the following general formula I:

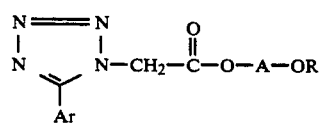

wherein in the formula I, R represents a hydrogen atom or a lower alkyl group; A is an alkylene group having 2 to 5 carbon atoms; Ar is selected from the group consisting of a phenyl group, a naphthyl group, a furyl group, a thienyl group, a benzofuryl group, and a benzothienyl group; wherein the Ar may be substituted with a lower alkyl group, a lower alkoxy group, a halogen atom, a lower haloalkyl group, an alkylthio group and an alkylsulfonylamino group shows excellent aldose reductase inhibitory activity, and is quite effective as an essential component of a preventive medicine and/or remedy for diabetic complications.

8 Claims, No Drawings

TETRAZOLEACETIC ACID DERIVATIVES AND METHOD OF ALDOSE REDUCTASE INHIBITION THEREWITH

BACKGROUND OF THE INVENTION

The present invention relates to a compound having an aldose reductase inhibitory activity and more specifically to a tetrazoleacetic acid derivative and an aldose reductase inhibitor which comprises the tetrazoleacetic acid derivative as an effective component and which is effective as a preventive medicine and/or remedy for diabetic complications as well as a method for alleviating or reducing diabetic complications.

It has been known that aldose reductase inhibitors are effective for prevention and/or treatment of diabetic complications. This is detailed in the article of Dr. Tsuyoshi TANIMOTO [Division of Biological Chemistry and Reference Standards, National Institute of Hygienic Sciences] Farumashia, 1988, 24, No. 5, pp. 459–463).

This article discloses the chemical structures and 50% inhibitory concentrations ($IC_{50}$) of representative aldose reductase inhibitors such as Alrestatin, Tolrestat, 4-Isopropyl-BPOC, Sorbinil, M-79175, Alconil, ADN-138, Epalrestat, CT-112 and Statil.

Metabolism, 28:456 (1979) and Jap. J. Opthalmol., 20:399 (1976) report that sorbitol accumulates in the lens or peripheral nerves of a patient suffering from diabetes by the action of aldose reductase, whereby causing diabetic complications.

The inventors of this invention have already conducted screening of novel aldose reductase inhibitors, found that tetrazoleacetic acid derivatives have very high aldose reductase inhibitory activity, and filed four patent applications. Among them, two patents were granted (U.S. Pat. Nos. 5,055,481 and 5,068,239). The other two are now pending (U.S. Ser. Nos. 07/821,456 and 07/857,400).

The co-inventors of the present application reported that a compound having a high aldose reductase inhibitory activity and having the general formula (III):

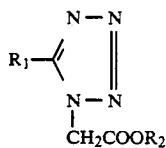

wherein $R_1$ means a ring of pyridine, pyrrole, furan, thiophene, benzofuran, benzothiophene, etc., by treating $R_1CONHCH_2COOR_2$ ($R_1$ is defined above) with $PCl_5$ or $SOCl_2$ in N, N-dimethylformamide (DMF), and then reacting the resultant compound with $NaN_3$ in DMF (Abstracts of The Papers at The 111th Anual Meeting of The Pharmaceutical Society of Japan, No. 2:220 (29 V), published on Mar. 5, 1991).

However, according to this method, a compound having the general formula (III), wherein an OR group (R is H or lower alkyl group) is introduced into the group $R_2$, was not able to be produced. In addition, the present inventors have found that by introducing the OR group into the $R_2$ group of the general formula (III), there is obtained a new 5-substituted tetrazoleacetic acid derivative which exhibits an aldose reductase inhibitory activity equivalent to or much higher than that of the compound wherein the OR group is not introduced into the $R_2$ group.

SUMMARY OF THE INVENTION

An object of the present invention is to provide a compound which shows excellent aldose reductase inhibitory activity, and is quite effective as a preventive medicine and/or remedy for diabetic complications and more specifically to provide a tetrazoleacetic acid derivative.

Another object of the present invention is to provide an aldose reductase inhibitor which comprises the tetrazoleacetic acid derivative as an effective component and which is effective as a preventive medicine and/or remedy for diabetic complications.

A further object of the present invention is to provide a method for alleviating or reducing symptoms related to diabetic complications.

According to an aspect of the present invention, there is provided a novel tetrazoleacetic acid derivative represented by the following general formula I.

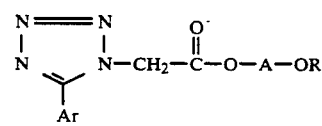

wherein in Formula I, R represents a hydrogen atom or a lower alkyl group; A is an alkylene group having 2 to 5 carbon atoms, Ar is selected from the group consisting of a phenyl group, a naphthyl group, a furyl group, a thienyl group, a benzofuryl group, and a benzothienyl group, wherein each of the groups represented by Ar may be substituted with a lower alkyl group, a lower alkoxy group, a halogen atom, a lower haloalkyl group, an alkylthio group, or an alkylsulfonylamino group.

According to another aspect of the present invention there is provided an aldose reductase inhibitor which comprises a tetrazoleacetic acid derivative represented by Formula I (in Formula I, R, A and Ar have the same meanings as above and Ar may be substituted with the same substituents above, and a pharmaceutical acceptable carrier.

DETAILED EXPLANATION OF THE INVENTION

The tetrazoleacetic acid derivatives and the aldose reductase inhibitor as well as the method for alleviating diabetic complications according to the present invention will hereunder be explained in more detail.

First, each substituent in Formula I will be explained in detail.

The lower alkyl group represented by R is, for instance, methyl, ethyl, propyl, isopropyl, butyl, isobutyl or t-butyl group.

Ar means a phenyl group, a naphthyl group, a furyl group, a thienyl group, a benzofuryl group or a benzothienyl group. The group Ar may have a substituent selected from the group consisting of a lower alkyl group, a lower alkoxy group, a halogen atom, a lower haloalkyl group, an alkylthio group, and an alkylsulfonylamino group.

The lower alkyl group as a substituent is for instance, methyl, ethyl, propyl, isopropyl, butyl, isobutyl or t-butyl group; the lower alkoxy group as a substituent is, for instance, methoxy, ethoxy, propoxy, isopropoxy, butoxy, isobutoxy, or t-butoxy group; the halogen atom as a substituent is, for instance, fluorine, chlorine or bromine; the lower haloalkyl group as a substituent is, for instance, mono-, di- or tri-haloalkyl group such as fluoromethyl, chloromethyl, bromomethyl or chlorobutyl group; the alkylthio group as a substituent is, for instance, methylthio, ethylthio, propylthio, butylthio or phenylthio group; the alkylsulfonylamino group as a substituent is, for instance, methylsulfonylamino, ethylsulfonylamino, propylsulfonylamino, butylsulfonylamino or phenylsulfonylamino group. These substituents may be substituted on any position on the group Ar.

The present compound (I) having the general formula I can be easily produced by the reaction of a compound (II) represented by the following general formula II:

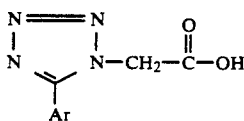

Ar is the same meaning as the above, with an alkylenediol or an alkylenediol monoalkyl ether. More specifically, the compound (I) can be obtained in high yield by the reaction of the compound (II) with an alkylenediol or an alkylenediol monoalkyl ether in the presence of acid catalyst, or condensation agent in an organic solvent.

In the case of using an acid catalyst, the amount of the alkylenediol or alkylenediol monalkyl ether to be used is not limited because it is used as a solvent. It is preferable that these compound be used in an amount of 2 to 5 times that of the compounds (II). The acid catalyst as a reaction accelerator may be conventional, for instance, sulfuric acid and p-toluene sulfonic acid, preferably sulfuric acid. The reaction temperature is 60° to 100° C., preferably 70°-90° C., and the reaction time is 2 to 5 hours, preferably 2 to 3 hours.

In the case of using a condensation agent, the solvent may be conventional, for instance, methylene chloride, chloroform, ethyl acetate and N,N-dimethylformamide, preferably N,N-dimethylformamide. The alkylenediol or alkylenediol monoalkyl ether is usually used in an amount of 1 to 2 moles, preferably 1. 2–1.5 moles of the compounds (II).

The condensation agent may also be conventional, for instance, dicyclohexylcarbodiimide and diethyl phosphoric cyanide, preferably dicyclohexylcarbodiimide. The amount of the condensation agent to be used is not limited. Generally, it is used in an amount of 1 to 2 moles, preferably 1.1 to 1.2 moles of the compound (II). The reaction temperature is generally room temperature or below room temperature, preferably 5° to 10° C. The reaction time is 0.5 to 3 hours, preferably 1 hour.

The specific examples of the compounds (II) are mentioned in for example U.S. Pat. Nos. 5,055,481 and 5,068,239.

The compounds (I) as prepared according to the foregoing method are separated and purified by a chemical operation commonly employed, such as extraction, recrystallization and/or column chromatography, and are used as essential compounds for the aldose inhibitors of the present invention.

The aldose reductase inhibitors according to the present invention comprise, as an essential component, at least one compound represented by the foregoing general formula I, and are effective as preventive medicines and/or remedies for diabetic complications. It has been known that the term "diabetic complications" means a variety of pathema such as peripheral disorder, retinopathy, nephrosis, cataract and keratopathy. These diseases or disorders are triggered by hyperglycemia resulted from the diabetic disease, whereby the production of sorbitol in the polyol metabolic pathway is correspondingly abnormally accelerated, and as a result, a large amount of sorbitol is accumulated within cells. This leads to the onset of these diseases.

The aldose reductase inhibitors of the present invention can suppress the sorbitol-production through strong inhibition of the activity of the aldose reductase which catalyzes the sorbitol-production in the foregoing polyol metabolic pathway and thus show excellent preventive and/or treating effects for these various diabetic complications.

The dose of the compounds of the formula I is appropriately determined depending on the conditions or symptoms of patients to be treated; but in general ranges from 1 to 1,000 mg per day for an adult which is administered at one time or over several times. The compounds may be administered through any route for medication, such as oral or parenteral administration, subcutaneous injection, intravenous injection and local administration.

The aldose reductase inhibitors of the present invention comprise pharmaceutically acceptable carriers, vehicles and other additives. The inhibitors of the invention may be used in any dosage form such as tablets, powders, fine particles, granules, capsules, pills, liquid preparations, solutions and suspensions for injection and eye drops.

The present invention will be hereinafter described in more detail with reference to the following non-limitative working Examples and Test Examples.

EXAMPLE 1

Preparation of [5-(3-thienyl)tetrazol-1-yl] acetic acid 2-hydroxyethyl ester

To a solution of 1 g (4.7 mM) of [5-(3-thienyl)tetrazol-1-yl] acetic acid in 5 ml of ethylene glycol was added 0.5 ml of sulfuric acid. After the addition, the mixture was stirred at 90° C. for 2.5 hrs. The mixture was then poured into ice-water and the precipitated crystal was filtered off, washed with water and recrystrallized from ethyl alcohol, to give 620 mg (yield 50%) of [5-(3-thienyl)tetrazol-1-yl] acetic acid 2-hydroxyethyl ester.

M.P.: 103°–106° C.

N.M.R.($CDCl_3$+DMSO-$d_6$) δ: 3.78(t,2H,J=4.62 Hz), 4.19(br,1H): 4.36(t,2H,J=4.64 Hz), 5.37(s,2H): 7.52(dd,1H,J=5.13,1.47 Hz): 7.56(dd,1H,J=5.13,2.83 Hz): 7.93(dd,1H,J=2.83,1.47 Hz).

I.R. $\nu_{KBr}$ cm$^{-1}$: 3330, 1740, 1570, 1230

Mass: m/z 254 [M+]

EXAMPLE 2

Preparation of [5-(2-methylthio-3-thienyl)tetrazol-1-yl]acetic acid 2-hydroxyethyl ester To a solution of 920 mg (3.6 mM) of [5-(2-methylthio-3-thienyl)tetrazol-1-yl]acetic acid in 5 ml of ethylene glycol was added 0.5 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=50/1) for separation and purification, to give 950 mg (yield 88.1%) of [5-(2-methylthio-3-thienyl)tetrazol-1-yl] acetic acid 2-hydroxyethyl ester.

N.M.R.(CDCl$_3$) δ: 2.48(s,3H), 3.80(t,2H,J=4.6 Hz); 4.28(t,2H,J=4.64 Hz), 5.25(s,2H); 7.17(d,1H,J=5.37 Hz); 7.46(d,1H,J=5.37 Hz).

I.R. $\nu_{NaCl}$cm$^{-1}$: 3400,2950,1750,1560,1440,1380, 1350,1220

Mass: m/z 300 [M+]

EXAMPLE 3

Preparation of [5-(2-thienyl)tetrazol-1-yl] acetic acid 2-hydroxyethyl ester

To a solution of a 1 g (4.7 mM) of [5-(2-thienyl)tetrazol-1-yl] acetic acid in 5 ml of ethylene glycol was added 0.5 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=50/1) for separation and purification, to give 1 g (yield 88.5%) of [5-(2-thienyl)tetrazol-1-yl] acetic acid 2-hydroxyethyl ester.

N.M.R.(CDCl$_3$) δ:3.84(m,2H),4.37(t,2H,J=4.52 Hz) 5.39(s,2H), 7.23(dd,1H,J=5.12,3.67 Hz), 7.60(dd,1H,J=3.67, 1.22 Hz), 7.65(dd,1H,J=5.12,1.22 Hz).

I.R. $\nu_{NaCl}$ cm$^{-1}$: 3400,1750,1570,1480,1440,1220
Mass : m/z 254 [M+]

EXAMPLE 4

Preparation of [5-[(3-methylsulfonylamino)-2-thienyl]tetrazol-1-yl] acetic acid 2-hydroxyethyl ester To a solution of 500 mg (1.6 mM) of [5-[(3-methylsulfonylamino)-2-thienyl]tetrazol-1-yl] acetic acid in 3 ml of ethylene glycol was added 0.3 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=30/1) for separation and purification, to give 420 mg (yield 73.3%) of [5-[(3-methylsulfonylamino)-2-thienyl]tetrazol-1-yl] acetic acid 2-hydroxyethyl ester.

M.P.: 107°-108° C.

N.M.R.(CDCl$_3$) δ: 3.08(s,3H),3.81(t,2H,J=4.64 Hz), 4.36(t,2H,J=4.64 Hz),5.50(s,2H), 7.57(d,1H,J=5.37 Hz), 7.62(d,1H,J=5.37 Hz), 9.94(br,1H).

I.R. $\nu_{KBr}$ cm$^{-1}$: 3400,3150,2940,1740,1560,1430, 1370,1320,1210

Mass: m/z 347 [M+]

EXAMPLE 5

Preparation of [5-[5-(3-phenylpropyl)-2-thienyl]tetrazol-1-yl]acetic acid 2-hydroxyethyl ester To a solution of 300 mg (0.9 mM) of [5-[5-(3-phenylpropyl)-2-thienyl]tetrazol-1-yl] acetic acid in 2 ml of ethylene glycol was added 0.2 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=30/1) for separation and purification, to give 300 mg (yield 88.2%) of [5-[5-(3-phenylpropyl)2-thienyl]tetrazol-1-yl] acetic acid 2-hydroxyethyl ester.

N.M.R. (CDCl$_3$) δ: 1.92(br,1H), 2.05(quint,2H,J=7.57 Hz), 2.71(t,2H,J=7.57 Hz), 2.90(t,2H,J=7.57 Hz), 3.82(dd,1H,J=9.27,5.37 Hz), 4.36(t,2H,J=4.64 Hz), 5.36(s,2H),6.90(d,1H,J=3.66 Hz), 7.17-7.35(m,5H), 7.43(d,1H,J=3.67 Hz).

I.R. $\nu_{Na\ Cl}$ cm$^{-1}$: 3400,2950,1750,1580,1510,1430, 1210

Mass: m/z 372 [M+]

EXAMPLE 6

Preparation of (5-phenyltetrazol-1-yl) acetic acid 2-hydroxyethyl ester

To a solution of 1 g (4.85 mM) of (5-phenyltetrazol-1-yl) acetic acid in 5 ml of ethylene glycol was added 0.5 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=9/1) for separation and purification, to give 630 mg (yield 51.8%) of (5-phenyltetrazol-1-yl) acetic acid 2-hydroxyethyl ester.

M.P.: 54°-55° C.

N.M.R. (CDCl$_3$) δ: 2.31(br,1H),3.82(br,2H), 4.34(t,2H,J=4.64 Hz),5.23(s,2H), 7.52-7.68(m,5H).

I.R. $\nu_{KBr}$ cm$^{-1}$: 3500,2950,1760,1460,1230,1080
Mass: m/z 246 [M+]

EXAMPLE 7

Preparation of [5-(4-butylphenyl)tetrazol-1-yl] acetic acid 2-hydroxyethyl ester To a solution of 1 g (3.84 mM) of [5-(4-butylphenyl) tetrazol-1-yl] acetic acid in 5 ml of ethylene glycol was added 0.5 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=9/1) for separation and purification, to give 550 mg (yield 47.4%) of [5-(4-butylphenyl) tetrazol-1-yl] acetic acid 2-hydroxyethyl ester.

N.M.R. (CDCl$_3$) δ: 0.94(t,3H,J=7.33 Hz), 1.33-1.58(m,2H), 1.61-1.69(m,2H),2.19(br,1H), 2.69(t,2H,J=7.69 Hz),3.83(br,2H), 4.34(t,2H,J=2.93 Hz),5.26(s,2H), 7.36(d,2H,J=8.06 Hz), 7.57(d,2H,J=8.43 Hz).

I.R. $\nu_{NaCl}$ cm$^{-1}$: 3400,2950,1760,1620,1480,1440, 1210,1080,760

Mass: m/z 302 [M+]

EXAMPLE 8

Preparation of [5-(4-butoxyphenyl)tetrazol-1-yl] acetic acid 2-hydroxyethyl ester To a solution of 0.5 g (1.81 mM) of [5-(4-butoxyphenyl) tetrazol-1-yl] acetic acid in 3 ml of ethylene glycol was added 0.3 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=20/1) for separation and purification, to give 400 mg (yield 69%) of [5-(4-butoxyphenyl) tetrazol-1-yl] acetic acid 2-hydroxyethyl ester.

N.M.R.(CDCl$_3$) δ: 0.99(t,3H,J=7.45 Hz), 1.44-1.58(m,2H), 1.75-1.86(m,2H), 2.08(t,1H,J=5.62 Hz), 3.83(br,2H),4.08(t,2H,J=6.47 Hz), 4.34(t,2H,J=4.64 Hz),5.24(s,2H), 7.03(dd,2H,J=6.84,2.20 Hz), 7.60(dd,2H,J=6.84,1.95 Hz).

I.R. $\nu_{NaCl}$ cm$^{-1}$: 3400,2950,1750,1610,1480,1250, 1210

Mass: m/z 320 [M+]

EXAMPLE 9

Preparation of [5-(4-fluorophenyl)tetrazol-1-yl] acetic acid 2-hydroxyethyl ester To a solution of 300 mg (1.35 mM) of [5-(4-fluorophenyl)tetrazol-1yl] acetic acid in 2 ml of ethylene glycol was added 0.2 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=25/1) for separation and purification, to give 290 mg (yield 80.7%) of [5-(4-fluorophenyl)tetrazol-1-yl] acetic acid 2-hydroxyethyl ester.

N.M.R.(CDCl$_3$) δ: 2.23(br,1H),3.84(br, 2H), 4.36(t,2H,J=4.64 Hz), 5.25(s,2H),7.22-7.30(m,2H), 7.66-7.71(m,2H),

I.R. $\nu_{NaCl}$ cm$^{-1}$: 3400,2950,1750,1600,1480,1440, 1220

Mass: m/z 266 [M+]

EXAMPLE 10

Preparation of [5-(3-trifluoromethylphenyl)tetrazol-1-yl] acetic acid 2-hydroxyethyl ester To a solution of 300 mg (1.10 mM) of [5-(3-trifluoromethylphenyl)tetrazol-1-yl] acetic acid in 2 ml of ethylene glycol was added 0.2 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=20/1) for separation and purification, to give 310 mg (yield 88.9%) of [5-(3-trifluoromethylphenyl)-tetrazol-1-yl] acetic acid 2-hydroxyethyl ester.

N.M.R.(CDCl$_3$) δ: 2.08(t,1H,J=5.50 Hz),3.85(br,2H), 4.36(t,2H,J=4.64 Hz),5.28(s,2H), 7.72(t,1H,J=7.69 Hz), 7.87-7.90(m,2H),7.97(s,1H).

I.R. $\nu_{NaCl}$ cm$^{-1}$: 3400,1750,1450,1340,1310,1260, 1210

Mass: m/z 316 [M+]

EXAMPLE 11

Preparation of [5-(2-naphthyl)tetrazol-1-yl] acetic acid 2-hydroxyethyl ester

To a solution of 1 g (3.94 mM) of [5-(2-naphthyl)tetrazol-1-yl] acetic acid in 5 ml of ethylene glycol was added 0.5 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=9/1) for separation and purification, to give 750 mg (yield 64.4%) of [5-(2-naphthyl)tetrazol-1-yl] acetic acid 2-hydroxyethyl ester.

M.P.: 64°-66° C.

N.M.R.(CDCl$_3$) δ: 2.16(t,1H,J=5.08 Hz),3.83(br,2H), 4.34(t,2H,J=4.58 Hz),5.32(s,2H), 7.56-7.66(m,2H), 7.71(dd,1H,J=8.43,1.83 Hz), 7.90-7.94(m,2H), 8.01(d,1H,J=8.43,1.83 Hz), 7.90-7.94(m,2H), 8.01(d,1H,J=8.79 Hz), 8.17(s,1H).

I.R. $\nu_{KBr}$ cm$^{-1}$: 3400,2920,1740,1290,1010,820,760

Mass: m/z 296 [M+]

EXAMPLE 12

Preparation of [5-(3-furyl)tetrazol-1-yl] acetic acid 2-hydroxyethyl ester

To a solution of 1 g (5.3 mM) of [5-(3-furyl)tetrazol-1-yl] acetic acid in 5 ml of ethylene glycol was aded 0.5 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatogrpahy (eluent: chloroform/methyl alcohol=50/1) for separation and purification to give 670 mg (yield 54.6%) of [5-(3-furyl)-tetrazol-1-yl] acetic acid 2-hydroxyethyl ester.

M.P.: 91°-93° C.

N.M.R. (CDCl$_3$) δ: 2.04(br, 1H),3.86(t,2H,J=4.64 Hz), 4.38(t,2H,J=4.64 Hz),5.29(s,2H), 6.83(dd,1H,J=1.95,0.97 Hz), 7.62(dd,1H,J=1.95,1.46 Hz), 8.00(dd,1H,J=1.46,0.97 Hz).

I.R. $\nu_{KBr}$ cm$^{-1}$: 3350,3100,1735,1620,1530,1440, 1220

Mass: m/z 238 M+]

EXAMPLE 13

Preparation of [5-(2-benzofuryl)tetrazol-1-yl]acetic acid 2-hydroxyethyl ester

To a solution of 2.4 g (9.8 mM) of [5-(2-benzofuryl) tetrazol-1-yl]acetic acid in 12 ml of ethylene glycol was added 1 ml of sulfuric acid. After the addition, the mixture was stirred at 90° C. for 2.5 hrs. The mixture was then poured into ice-water and the precipitated crystal was filtered off, washed with water and then dissolved in ethyl acetate. The organic solution was dried over anhydrous magnesium sulfate and then concentrated under reduced pressure. The resultant residue was recrystallized from methyl alcohol, to give 2.14 g (yield 75.4%) of [5-(2-benzofuryl)tetrazol-1-yl]acetic acid 2-hydroxyethyl ester.

M.P.: 131°–135° C.

N.M.R.($CDCl_3$+DMSO-$d_6$) δ: 3.82(t,2H,J=4.64 Hz), 4.34(t,2H,J=4.64 Hz), 5.66(s,2H),7.33–7.39(m,1H), 7.42–7.49(m,1H), 7.56(dd,1H,J=8.30,0.73 Hz), 7.72–7.75(m,2H).

I.R. $\nu_{KBr}$ cm$^{-1}$: 3350,2950,1760,1620,1440,1380, 1220

Mass: m/z 288 [M+]

EXAMPLE 14

Preparation of [5-(6-benzo[b]thienyl)tetrazol-1-yl]acetic acid 2-hydroxyethyl ester To a solution of 400 mg (1.54 mM) of [5-(6-benzo[b]thienyl)tetrazol-1-yl] acetic acid in 3 ml of ethylene glycol was added 0.3 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/methyl alcohol=50/1) for separation and purification, to give 400 mg (yield 85.5%) of [5-(6-benzo[b]thienyl)tetrazol-1-yl]acetic acid 2-hydroxyethyl ester.

N.M.R.($CDCl_3$) δ: 2.58(br,1H),3.81(br,2H), 4.34(t,2H,J=4.64 Hz),5.30(s,2H), 7.41(d,1H,J=5.37 Hz), 7.60(dd,1H,J=8.30,1.46 Hz), 7.64(d,1H,J=5.37 Hz), 7.95(d,1H,J=8.30 Hz), 8.21(t,1H,J=0.73 Hz),

I.R. $\nu_{NaCl}$ cm$^{-1}$: 3400,2950,1750,1530,1440,1380, 1210

Mass: m/z 304 [M+]

EXAMPLE 15

Preparation of [5-(3-thienyl)tetrazol-1-yl]acetic acid 3-hydroxypropyl ester

To a solution of 500 mg (2.38 mM) of [5-(3-thienyl) tetrazol-1-yl] acetic acid and 220 mg (2.85 mM) of 1,3-propanediol in 5 ml of N,N-dimethylformamide was added 540 mg (2.62 mM) of dicyclohexylcarbodiimide at room temperature. After the mixture was stirred at room temperature for 30 min, a small amount of acetic acid was added to the mixture and then was stirred for 30 min. The mixture was poured into ice-water. The precipitated crystal was filtered off and washed with water. The filtrate was extracted with ethyl acetate. The organic phase was washed with water, dried over anhydrous magnesium sulfate and then concentrated under reduced pressure. The resultant residue was subjected to silica gel column chromatography (eluent: chloroform/ethyl alcohol=60/1) for separation and purification, to give 350 mg (yield 54.8%) of [5-(3-thienyl) tetrazol-1-yl] acetic acid 3-hydroxypropyl ester.

N.M.R.($CDCl_3$) δ: 1.87(quint,2H,J=6.10 Hz), 3.65(t,2H,J=6.10 Hz), 4.38(t,2H,J=6.22 Hz),5.29(s,2H), 7.48(dd,1H,J=5.12,1.22 Hz), 7.56(dd,1H,J=5.12,2.69 Hz), 7.87(dd,1H,J=2.69,1.22 Hz).

I.R. $\nu_{Na\,Cl}$ cm$^{-1}$: 3400,2940,1740,1570,1430,1350, 1210

Mass: m/z 268 [M+]

EXAMPLE 16

Preparation of [5-(3-thienyl)tetrazol-1-yl]acetic acid 4-hydroxybutyl ester

To a solution of 1 g (4.76 mM) of [5-(3-thienyl)tetrazol-1-yl] acetic acid and 514 mg (5.71 mM) of 1,4-butanediol in 10 ml of N,N-dimethylformamide was added 1.08 g (5.23 mM) of dicyclohexylcarbodiimide at room temperature. After the mixture was stirred at room temperature for 30 min, a small amount of acetic acid was added to the mixture and then was stirred for 30 min. The mixture was poured into ice-water. The precipitated crystal was filtered off and washed with water. The filtrate was extracted with ethyl acetate. The organic phase was washed with water, dried over anhydrous magnesium sulfate and then concentrated under reduced pressure. The resultant residue was subjected to silica gel column chromatography (eluent: chloroform/ethyl alcohol=30/1) for separation and purification, to give 810 mg (yield 60.3%) of [5-(3-thienyl)tetrazol-1-yl] acetic acid 4-hydroxybutyl ester.

N.M.R.($CDCl_3$) δ:1.49–1.78(m,4H),3.64(br,2H), 4.26(t,2H,J=6.35 Hz),5.27(s,2H), 7.48(dd,1H,J=5.12, 1.46 Hz), 7.56(dd, 1H,J=5.12,2.93 Hz), 7.86(dd, 1H,J=2.93, 1.46 Hz),

I.R. $\nu_{Na\,Cl}$ cm$^{-1}$: 3400, 2940, 1740, 1570, 1210

Mass: m/z 282 [M+]

EXAMPLE 17

Preparation of [5-(3-thienyl)tetrazol-1-yl]acetic acid 4-hydroxybutyl ester

To a suspension of 1 g (4.76 mM) of [5-(3-thienyl) tetrazol-1-yl]acetic acid and 514 mg (5.71 mM) of 1,4-butanediol in 20 ml of ethyl acetate was added 1.08 g (5.23 mM) of dicyclohexylcarbodiimide at room temperature. After the mixture was stirred at room temperature for 30 min, a small amount of acetic acid was added to the mixture and then was stirred for 30 min. The mixture was filtered off and washed with ethyl acetate. The filtrate was concentrated under reduced pressure. The resultant residue was subjected to silica gel column chromatography (eluent; chloroform/ethyl alcohol=30/1) for separation and purification, to give 520 mg (yield 38.7%) of [5-(3-thienyl)tetrazol-1-yl]acetic acid 4-hydroxybutyl ester.

The elemental analysis and spectral data are the same as those in Example 16.

EXAMPLE 18

Preparation of [5-(3-thienyl)tetrazol-1-yl]acetic acid 5-hydroxypentyl ester

To a solution of 1 g (4.76 mM) of [5-(3-thienyl)tetrazol-1-yl]acetic acid and 590 mg (5.71 mM) of 1,5-pentanediol in 10 ml of N,N-dimethylformamide was added 1.08 g (5.23 mM) of dicyclohexylcarbodiimide at room temperature. After the mixture was stirred at room temperature for 30 min, a small amount of acetic acid was added to the mixture and then was stirred for 30 min. The mixture was poured into ice-water. The precipitated crystal was filtered off and washed with water. The filtrate was extracted with ethyl acetate. The organic phase was washed with water, dried over anhydrous magnesium sulfate and then concentrated under reduced pressure. The resultant residue was subjected to silica gel column chromatography (eluent: chloroform/ethyl alcohol=60/0) for separation and purification, to give 670 mg (yield 47.5%) of [5-(3-thienyl)tetrazol-1-yl]acetic acid 5-hydroxypentyl ester.

M.P.: 39°-42° C.

N.M.R.(CDCl$_3$) δ: 1.38-1.79(m,6H),3.71(br,2H)2, 4.31(t,2H,J=6.59 Hz),5.35(s,2H), 7.57(dd,1H,J=5.13,1.22 Hz), 7.64(dd,1H,J=5.13,2.93 Hz), 7.94(dd,1H,J=2.93,1.22 Hz).

I.R. $v_{KBr}$ cm$^{-1}$: 3400,2930,1740,1570,1430,1220

Mass: m/z 296 [M+]

EXAMPLE 19

Preparation of [5-(3-thienyl)tetrazol-1-yl]acetic acid 2-methoxyethyl ester

To a solution of 2 g (9.51 mM) of [5-(3-thienyl)tetrazol-1-yl]acetic acid in 10 ml of 2-methoxyethanol was added 1 ml of sulfuric acid. After the addition, the mixture was stirred at 90° C. for 2.5 hrs. The mixture was then poured into ice-water and extracted with ethyl acetate. The organic phase was washed with water, dried over anhydrous magnesium sulfate and then concentrated under reduced pressure. The resultant residue was subjected to silica gel column chromatography (eluent: chloroform/ethyl alcohol=30/1) for separation and purification, to give 2.1 g (yield 82.3%) of [5-(3-thienyl)tetrazol-1-yl]acetic acid 2-methoxyethyl ester.

N.M.R.(CDCl$_3$) δ: 3.35(s,3H),3.59(t,2H,J=4.64 Hz), 4.40(t,2H,J=4.64 Hz),5.29(s,2H), 7.49(dd,1H,J=5.13,1.47 Hz), 7.54(dd,1H,J=5.13,2.93 Hz), 7.87(dd,1H,J=2.93,1.47 Hz).

I.R. $v_{NaCl}$ cm$^{-1}$: 1750,1580,1440,1220

Mass: m/z 268 [M+]

The compounds prepared in the foregoing Examples are listed in the following Table 1.

TABLE 1

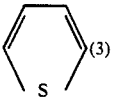

| Example | Ar | A | R |
|---|---|---|---|
| 1 | 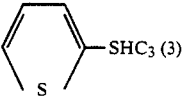 3-thienyl (3) | CH$_2$CH$_2$ | H |
| 2 | 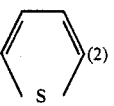 thienyl-SHC$_3$ (3) | CH$_2$CH$_2$ | H |
| 3 | 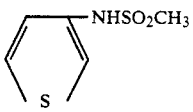 2-thienyl (2) | CH$_2$CH$_2$ | H |
| 4 | 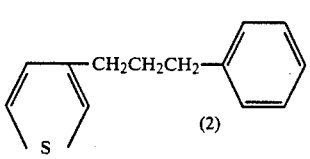 thienyl-NHSO$_2$CH$_3$ (2) | CH$_2$CH$_2$ | H |
| 5 |  thienyl-CH$_2$CH$_2$CH$_2$-phenyl (2) | CH$_2$CH$_2$ | H |
| 6 | 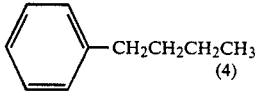 phenyl | CH$_2$CH$_2$ | H |
| 7 | phenyl-CH$_2$CH$_2$CH$_2$CH$_3$ (4) | CH$_2$CH$_2$ | H |
| 8 | 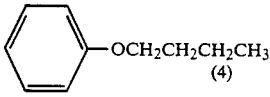 phenyl-OCH$_2$CH$_2$CH$_2$CH$_3$ (4) | CH$_2$CH$_2$ | H |

TABLE 1-continued $$\underset{Ar}{\underset{N}{\overset{N}{\underset{\|}{\bigg\|}}}\overset{N}{\underset{N-CH_2-\overset{O}{\overset{\|}{C}}-O-A-OR}{\bigg|}}}$$

| Example | Ar | A | R |
|---------|----|---|---|
| 9 | phenyl-F (4) | CH$_2$CH$_2$ | H |
| 10 | phenyl-CF$_3$ (3) | CH$_2$CH$_2$ | H |
| 11 | naphthyl (2) | CH$_2$CH$_2$ | H |
| 12 | furyl (3), O | CH$_2$CH$_2$ | H |
| 13 | benzofuryl (2), O | CH$_2$CH$_2$ | H |
| 14 | benzothienyl (6), S | CH$_2$CH$_2$ | H |
| 15 | thienyl (3), S | CH$_2$CH$_2$CH$_2$ | H |
| 16 | thienyl (3), S | CH$_2$CH$_2$CH$_2$CH$_2$ | H |
| 17 | thienyl (3), S | CH$_2$CH$_2$CH$_2$CH$_2$ | H |
| 18 | thienyl (3), S | CH$_2$CH$_2$CH$_2$CH$_2$CH$_2$ | H |
| 19 | thienyl (3), S | CH$_2$CH$_2$ | CH$_3$ |

Each number means the position of the Ar at which the Ar is bonded to the 5-position of the tetrazolyl group.

The pharmaceutical properties of the present compounds will be explained by way of the following tests.

Experiment 1

Aldose Reductase Inhibition Test
(1) Test Procedure

Six-week-old male SD rats were anesthetized with ether and killed. The their crystalline lenses were immediately removed and stored at $-80°$ C. The lenses were homogenized in 3 volumes of 135 mM sodium potassium phosphate buffer (pH 7.0) and centrifuged at 30,000 rpm for 30 minutes. The resulting supernatant was dialyzed overnight against 0.05M sodium chloride solution to obtain an aldose reductase solution. All operations were conducted at $4°$ C. and the enzyme solution was stored at $-80°$ C.

The activity of aldose reductase was determined according to a partially modified method of J. H. Kinoshita et al. (J. Biol. Chem., 1965, 240, p. 877). More specifically, 0.1 ml of DL-glyceraldehyde (final concentration: 10 mM) was added to 0.9 ml of 100 mM sodium potassium phosphate buffer (pH 6.2) which contained lithium sulfate (final concentrationL 400 mM), reduced nicotinamide adenine dinucleotide phosphate (final concentration: 0.15 mM), the enzyme solution, and the compound to be evaluated (final concentration: $10^{-5}$M, $10^{-6}$M, $10^{-7}$M or $10^{-8}$M), and then the reaction was conducted at $30°$ C. for 5 minutes. During the reaction, the change in the absorbance at 340 nm with time was monitored.

The maximum reducing rate of the absorbance (U) during the reaction was determined. By subtracting, from this value, the maximum reducing rate ($U_0$) at 340 nm of the reaction solution before the addition of the substrate (DL-glyceraldehyde), the reaction rate ($V=U-U_0$) was calculated as a true reaction rate in the presence of the compound to be tested.

The same procedure was repeated except for the absence of the compound to be tested. A true reaction rate ($V_0$) in case the enzyme was not inhibited was calculated ($V_0=U^1-U_0^1$). The aldose reductase inhibitory activity of the test compounds was determined according to the following formula:

Rate of Inhibition (%)=$(V_0-V)/V_0\times 100$

The concentration of inhibitor giving 50% inhibition of enzyme activity ($IC_{50}$) was estimated from the least-square regression line of the log dose-response curve.

For comparison, the same tests were conducted using a known aldose reductase inhibitor: ONO-2235 [(E)-3-carboxymethyl-5-[(2E)-methyl-30 phenylpropenylidene]rhodan].

(2) Results

The results of Experiment 1 are shown in Table 2. The results show that the present compounds provide excellent aldose reductase inhibitory activity.

TABLE 2

| Compound Tested (Example No.) | $IC_{50}$ ($\times 10^{-7}$ M) |
|---|---|
| 1 | 3.6 |
| 6 | 31 |
| 12 | 3.6 |
| 16 | 3.9 |
| 18 | 13 |
| 19 | 2.1 |
| ONO-2235 | 0.31 |

Experiment 2
Inhibitory activity test against sorbitol accumulation in sciatic nerve and lens
(1) Test Procedure Groups of 6 to 8-week-old Sprague-Dawley male rats (4 animals per group) were fasted for 18 hours and streptozotocin was injected through the tail vein in a dose of 60 mg/kg, to obtain diabetic rats.

Immediately after the administration of streptozotocin, each compound to be tested was orally administered to these rats in the form of a suspension at a dose of 5 mg/kg, 10 mg/kg and 100 mg/kg (each was suspended in a 0.5% sodium carboxymethyl cellulose solution) once a day (at 9 a.m.) for 5 days.

During the test, the rats took diet and drank water freely. Four hours after the final administration of the drug in the 5th day's morning (at 9 a.m.), the rats were sacrificed and then the sciatic nerve and lens were removed to determine the amounts of sorbitol accumulated therein.

The results are expressed in the percentage obtained when the value obtained on the control to which no drug was administered is defined 100.

For comparison, the same tests were conducted using a known aldose reductase inhibitor, ONO-2235.

(2) Results

The results thus obtained are summarized in Table 3 below. As seen from Table 2, the compounds of the present invention tested show, as a whole, aldose reductase inhibitory effect equivalent to or superior to those attained by the known inhibitor ONO-2235.

TABLE 3

| Compound tested (Example No.) | Rate of Inhibition of Sorbitol Accumulation (%) | | |
|---|---|---|---|
| | Sciatic nerve | | lens |
| | 5 mg/kg | 10 mg/kg | 100 mg/kg | 100 mg/kg |
| 1 | 48 | 73 | 102 | 50 |
| 6 | 29 | 46 | 103 | 24 |
| 12 | 41 | 70 | 107 | 68 |
| 15 | 24 | 37 | 110 | 36 |
| 16 | −5 | 35 | 103 | −10 |
| 18 | −27 | 16 | 102 | 7 |
| 19 | 22 | 38 | 103 | 13 |
| ONO-2235 | 0 | 0 | 40 | — |

As comparative test data, the pharmaceutical properties of the compounds III having the general formula III ($R_2$ is H or a lower alkyl group), which compounds were reported in The Pharmaceutical Society of Japan, the 111th Anual Meeting (1991), are listed in Table 4 below.

TABLE 4

$$R_1-\underset{\underset{CH_2COOR_2}{|}}{\overset{N-N}{\underset{N-N}{\|}}}\quad\quad III$$

| Comparative Compound | $R_1$ | $R_2$ | Rate of Inhibition of Sorbitol Accumulation (%) in Sciatic Nerve (10 mg/kg) |
|---|---|---|---|
| 1 | (thiophene) | H | 53 |
| 2 | (thiophene) | $C_2H_5$ | 63 |

TABLE 4-continued $$
\underset{\substack{|\\CH_2COOR_2}}{\overset{N-N}{R_1-\!\!\!\!\bigg\langle\begin{array}{c}\|\\\|\\N-N\end{array}}}
\quad III
$$

| Comparative Compound | $R_1$ | $R_2$ | Rate of Inhibition of Sorbitol Accumulation (%) in Sciatic Nerve (10 mg/kg) |
|---|---|---|---|
| 3 | ⟨S⟩ (3) | H | 35 |
| 4 | ⟨O⟩ (3) | H | 40 |
| 5 | ⟨phenyl⟩ | H | 40 |

By comparing the results in Table 4 with those in Table 2, it is apparent that by introducing the OR group into the alkyl ester moiety of the tetrazoleacetic acid compound (III), the rate of inhibition of sorbitol accumulation (%) in sciatic nerve is much improved. For example, by comparing the compound of Example 1 with Comparative compound No. 2 (the difference in chemical structure therebetween is the addition of a hydroxy group to a methyl group), the present compound increases the sorbitol accumulation rate (%) from 63% (the comparative compound) to 73%. This increases is remarkable in light of the pharmaceutical property.

As has been explained above in detail, the aldose reductase inhibitor of the present invention shows excellent aldose reductase inhibitory activity. Therefore, it can be used as a medicine for preventing and/or treating a mammalian inclusive of a man suffering from diabetic complications, such as neural disorders, nephrosis, cataract and retinopathy, with safety.

What is claimed is:

1. A tetrazoleacetic acid derivative represented by the general formula I:

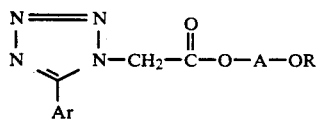

wherein in the formula I, R represents a hydrogen atom or a lower alkyl group; A is an alkylene group having 2 to 5 carbon atoms; Ar is selected from the group consisting of a phenyl group, a naphthyl group, a furyl group, a thienyl group, a benzofuryl group, and a benzothienyl group, wherein the Ar may be substituted with a lower alkyl group, a lower alkoxy group, a halogen atom, a lower haloalkyl group, a alkylthio group and an alkylsulfonylamino group.

2. The tetrazoleacetic acid derivative of claim 1 wherein, in the formula I, the lower alkyl group as R is selected from the group consisting of methyl, ethyl, propyl, isopropyl, butyl, isobutyl or t-butyl group; the lower alkyl group as a substituent on the Ar is selected from the group consisting of methyl, ethyl, propyl, isopropyl, butyl, isobutyl and t-butyl; the lower alkoxy group as a substituent on the Ar is selected from the group consisting of methoxy, ethoxy, propoxy, isopropoxy, butoxy, isobutoxy and t-butoxy; the halogen atom as a substituent on the Ar is selected from the group consisting of fluorine, chlorine and fromine; the lower haloalkyl group as a substituent on the Ar is selected from the group consisting of mono-, di- or tri-fluoromethyl, chloromethyl, bromomethyl and chlorobutyl group; the alkylthio group as a substituent on the Ar is selected from the group consisting of methylthio, ethylthio, propylthio, butylthio andphenylthio group; and the alkylsulfonylamino group as a substituent on the Ar is selected from the group consisting of methylsulfonylamino, ethylsulfonylamino, propylsulfonylamino, butylsulfonylamino and phenylsulfonylamino group.

3. An aldose reductase inhibitor comprising a tetrazoleacetic acid derivative represented by the general formula I:

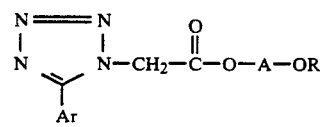

wherein in the formula I, R represents a hydrogen atom or a lower alkyl group; A is an alkylene group having 2 to 5 carbon atoms; Ar is selected from the group consisting of a phenyl group, a naphthyl group, a furyl group, a thienyl group, a benzofuryl group, and a benzothienyl group, wherein the Ar may be substituted with a lower alkyl group, a lower alkoxy group, a halogen atom, a lower haloalkyl group, an alkylthio group and an alkylsulfonylamino group and a pharmaceutically carrier.

4. The aldose reductase inhibitor of claim 3 wherein, in the formula I, the lower alkyl group as R is selected from the group consisting of methyl, ethyl, propyl, isopropyl, butyl, isobutyl and t-butyl group; the lower alkyl group as a substituent on the Ar is selected from the group consisting of methyl, ethyl, propyl, isopropyl, butyl, isobutyl and t-butyl group; the lower alkoxy group as a substituent on the Ar is selected from the group consisting of methoxy, ethoxy, propoxy, isopropoxy, butoxy, isobutoxy, and t-butoxy group; the halogen atom as a substituent on the Ar is selected from the group consisting of fluorine, chlorine and bromine; the lower haloalkyl group as a substituent on the Ar is selected from the group consisting of mono-, di- or tri-fluoromethyl, chloromethyl, bromomethyl and chlorobutyl group; the alkylthio group as a substituent on the Ar is selected from the group consisting of methylthio, ethylthio, propylthio, butylthio and phenylthio group; and the alkylsulfonylamino group as a substituent on the Ar is selected from the group consisting of methylsulfonylamino, ethylsulfonylamino, propylsulfonylamino, butylsulfonylamino and phenylsulfonylamino group.

5. A method for alleviating or reducing diabetic complications wherein a tetrazoleacetic acid derivative represented by the general formula I:

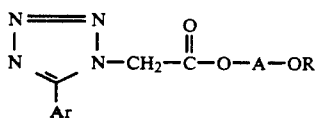

wherein in the formula I R represents a hydrogen atom or a lower alkyl group; A is an alkylene group having 2 to 5 carbon atoms; Ar is selected from the group consisting of a phenyl group, a naphthyl group, a furyl group, a thienyl group, a benzofuryl group, and a benzothienyl group; wherein the Ar may be substituted with a lower alkyl group, a lower alkoxy group, a halogen atom, a lower haloalkyl group, an alkylthio group and an alkylsulfonylamino group is used.

6. The method of claim 5 wherein, in the formula I, the lower alkyl group as R is selected from the group consisting of methyl, ethyl, propyl, isopropyl, butyl, isobutyl and t-butyl group; the lower alkyl group as a substituent on the Ar is selected from the group consisting of methyl, ethyl, propyl, isopropyl, butyl, isobutyl and t-butyl group; the lower alkoxy group as a substituent on the Ar is selected from the group consisting of methoxy, ethoxy, propoxy, isopropoxy, butoxy, isobutoxy, and t-butyl group; the halogen atom as a substituent on the Ar is selected from the group consisting of fluorine, chlorine and bromine; the lower haloalkyl group as a substituent on the Ar is selected from the group consisting of mono-, di- or tri-fluoromethyl, chloromethyl, bromomethyl and chlorobutyl group; the alkylthio group as a substituent on the Ar is selected from the group consisting of methylthio, ethylthio, propylthio, butylthio and phenylthio group; and the alkylsulfonylamino group as a substituent on the Ar is selected from the group consisting of methylsulfonylamino, ethylsulfonylamino, propylsulfonylamino, butylsulfonylamino and phenylsulfonyl amino group.

7. The method of claim 5 wherein the compound of the formula I is administered, at one time or over several times, in an amount ranging from 1 to 1,000 mg per day for adult, orally, subcutaneously, intravenously or locally.

8. The method of claim 5 wherein the compound of the formula I is administered in the form of tablets, powder, fine particles, granules, capsules, pills, liquid preparation, solutions or suspensions for injection or eye drops.

* * * * *